US007670326B2

(12) United States Patent
Shemesh

(10) Patent No.: US 7,670,326 B2

(45) Date of Patent: Mar. 2, 2010

(54) SYRINGE ADAPTER ELEMENT IN DRUG MIXING SYSTEM

(75) Inventor: Eli Shemesh, Ashdod (IL)

(73) Assignee: Teva Medical Ltd.., Ashdod (IL)

( * ) Notice: Subject to any disclaimer, the term of this patent is extended or adjusted under 35 U.S.C. 154(b) by 728 days.

(21) Appl. No.: 11/526,061

(22) Filed: Sep. 25, 2006

(65) Prior Publication Data

US 2008/0097371 A1 Apr. 24, 2008

(51) Int. Cl.
*A61B 19/00* (2006.01)

(52) U.S. Cl. ....................................... 604/415; 604/414

(58) Field of Classification Search ................. 604/403, 604/411, 414, 415

See application file for complete search history.

(56) References Cited

U.S. PATENT DOCUMENTS 6,478,788 B1 * 11/2002 Aneas ........................ 604/411
6,571,837 B2 * 6/2003 Jansen et al. ................ 141/329
6,706,031 B2 * 3/2004 Manera ...................... 604/411
2005/0203481 A1 * 9/2005 Orlu et al. ................... 604/411

* cited by examiner

*Primary Examiner*—Leslie R Deak
(74) *Attorney, Agent, or Firm*—Dekel Patent Ltd; David Klein

(57) ABSTRACT

A syringe adapter element for use in a drug mixing system including a housing element having a syringe port adapted for fluid connection with a syringe and a fluid port adapted for fluid connection with a fluid flow adapter element, a needle and at least one septum disposed in the housing element, the needle having a sealed orientation wherein the at least one septum blocks fluid flow through the needle and a fluid flow orientation wherein the needle punctures the at least one septum so as to permit fluid to flow through the needle, and an anti-separation device adjacent the fluid port, such that when the syringe adapter element is connected to a fluid flow adapter element, the anti-separation device applies a force that acts against separating the syringe adapter element from the fluid flow adapter element.

6 Claims, 7 Drawing Sheets

SYRINGE ADAPTER ELEMENT IN DRUG MIXING SYSTEM

FIELD OF THE INVENTION

The present invention relates to drug mixing systems generally and particularly to a safety feature that prevents rapid and sudden separation of a fluid flow adapter element from the syringe adapter element

BACKGROUND OF THE INVENTION

Drug mixing systems are well known in the art. One particular drug mixing system is described in published PCT patent application WO 2005/041846, assigned to the current assignee of the present application, the disclosure of which is incorporated herein by reference. The drug mixing system is commercially available from Teva Medical Ltd. and is sold under the brand name Tevadaptor. It is a system for safe compounding and administration of hazardous intravenous drugs. Tevadaptor minimizes the risk of exposure to hazardous drug substances, and eliminates the risk of needle stick injuries. The drug mixing system is intended for use with a luer fitted hypodermic syringe, and is particularly useful for handling toxic drugs such as antineoplastic drugs.

The Tevadaptor drug mixing system includes a receptacle port adapter that can be inserted into a port of a fluid receptacle, such as an IV bag. A vial adapter element is provided for connection to a vial containing a drug. A syringe adapter element may be attached to a syringe and to the receptacle port adapter and/or the vial adapter element. The receptacle port adapter, syringe adapter element and/or the vial adapter element may be vented to the atmosphere in a manner that prevents release to the atmosphere of possibly harmful contents of the vial in a liquid, solid or gaseous form.

The syringe adapter element may have a needle that fluidly communicates with the contents of the syringe. The needle does not normally protrude outwards, but rather is sealed inside the syringe adapter element by a septum. The syringe adapter element may be screwed onto the luer lock tip of the syringe. The needle of the syringe adapter element is now in fluid communication with the contents of the syringe.

Similarly, the vial adapter element may have a spike that fluidly communicates with the contents of the vial, and is sealed by a septum. The vial may be pushed onto the vial adapter element, wherein the spike of the vial adapter element punctures the septum of the vial. The vial adapter element may then be pushed onto the syringe adapter element, wherein the needle of the syringe adapter element punctures the septa of the syringe adapter element and the vial adapter assembly. This allows fluid to flow from the syringe through the needle of the syringe adapter element and through the spike of the vial adapter element to the vial.

After filling the vial with a desired amount of fluid, the vial adapter assembly may be separated from the syringe adapter element. Immediately upon separation, the needle of the syringe adapter element retracts inwards and is sealed by elastomeric septa. In this manner, no fluid drips outwards.

SUMMARY OF THE INVENTION

The present invention seeks to provide further features to a drug mixing system, particularly a further safety feature that prevents premature separation of a fluid flow adapter septum element from the syringe adapter septum element. This safety feature may further ensure that no fluid drips outward when separating these parts from one another.

There is thus provided in accordance with an embodiment of the present invention a syringe adapter element for use in a drug mixing system including a housing element having a syringe port adapted for fluid connection with a syringe and a fluid port adapted for fluid connection with a fluid flow adapter element, a needle and at least one septum disposed in the housing element, the needle having a sealed orientation wherein the at least one septum blocks fluid flow through the needle, and a fluid flow orientation wherein the needle punctures the at least one septum so as to permit fluid to flow through the needle, and an anti-separation device adjacent the fluid port, such that when the syringe adapter element is connected to a fluid flow adapter element, the anti-separation device applies a force that acts against separating the syringe adapter septum element from the fluid flow adapter septum element.

In accordance with an embodiment of the present invention the anti-separation device includes a ring member with a plurality of resilient leaves disposed inside a keeper element, the keeper element having a first bore sized to prevent outward expansion of the resilient leaves and a second bore, larger than the first bore, sized to permit outward expansion of the resilient leaves, the resilient leaves being adapted to resiliently fasten onto a fluid flow adapter element, the anti-separation device having first and second positions, wherein in the first position, the resilient leaves are positioned in the first bore and are adapted to hold onto the fluid flow adapter element, and in the second position, the resilient leaves are positioned in the second bore and are adapted to expand outward to release the fluid flow adapter element.

In accordance with another embodiment of the present invention the anti-separation device includes a plurality of inwardly facing protrusions formed on an inner perimeter of the fluid port adapted to apply a friction force against a fluid flow adapter element inserted in the fluid port.

In accordance with yet another embodiment of the present invention the anti-separation device includes at least one non-straight channel formed in one of the fluid flow adapter elements that interfaces with a tooth formed in the other of the syringe adapter and fluid flow adapter elements, wherein a axial force applied to separate the syringe adapter and fluid flow adapter elements is acted against by the tooth moving in the non-straight channel.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figures 1, 2:
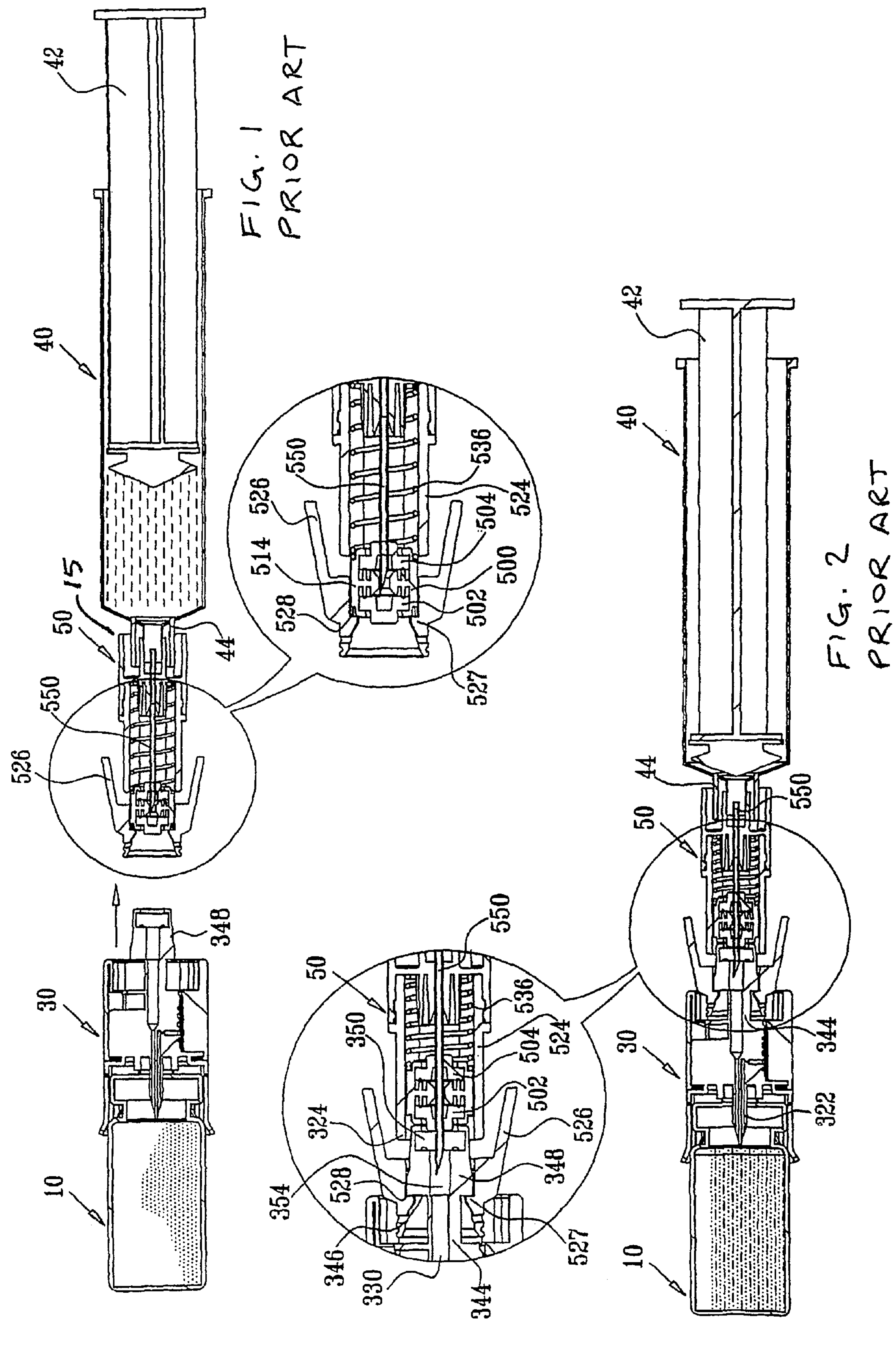
FIG. 1 PRIOR ART
FIG. 2 PRIOR ART
FIGS. 1 and 2 are partially sectional illustrations of a drug mixing system of the prior art, respectively with a vial adapter assembly connected and disconnected to a syringe adapter element.

Reference is now made to FIGS. 1 and 2, which illustrate a drug mixing system of the prior art, such as that described in published PCT patent application WO 2005/041846.

The drug mixing system may include a luer fitted hypodermic syringe 40 having a plunger 42 and a luer tip 44, which can be attached to a syringe port 15 of a syringe adapter element 50.

Syringe adapter element 50 may include a housing element 500, which has seated therein a forward septum 502 and a rearward septum 504 in an intermediate portion 514. Syringe adapter element 50 may include a body 524 in which a spring 536 and needle 550 are disposed. Extending from body 524 are outwardly protruding arms 526, defining at an inner facing forward end thereof teeth 527 having transversely extending rearward facing surfaces 528 which engage with intermediate portion 514. Needle 550 may extend axially within compression spring 536 and through the center of axially movable housing element 500 and rearward septum 504. A sharpened tip of needle 550 may be placed between forward septum 502 and rearward septum 504, thus maintaining the needle inaccessible to a user and to the atmosphere.

The drug mixing system allows connecting syringe adapter element 50 to different adapter elements, such as but not limited to, a vial adapter element 30, a spike port adapter element (not shown) or needle port adapter element (also not shown). For example, connecting syringe adapter element 50 to either the spike port adapter element or the needle port adapter element permits fluid to flow through the spike port adapter element or through the needle port adapter element directly into syringe 40 via the syringe adapter element 50. This ensures that the fluid remains sterile, and that the user is not exposed to the fluid. Subsequently, the syringe 40 and syringe adapter element 50 may be disconnected from the spike port adapter element or the needle port adapter element. The drug mixing system ensures that the user is not exposed to the fluid during disconnection thereof.

The present invention will be described with particular reference to connection between the syringe adapter element 50 and the vial adapter element 30, but it is appreciated that the invention is applicable for connection of the syringe adapter element 50 to any of the abovementioned adapter elements. These adapter elements will be referred to alternatively in the specification and claims as fluid flow adapter elements.

As seen in FIG. 1, a user can connect syringe adapter element 50, which is attached to syringe 40, to a forward facing portion 348 of a vial adapter element 30 to which a vial 10 is connected.

The vial adapter element 30 may include a hollow vial puncturing spike 322 that extends (FIG. 2) rearwardly from a rearward surface 324 of the assembly. In the illustrated embodiment, an axial hollow tubular portion 330 is in fluid flow engagement with vial puncturing spike 322. A hollow neck portion 344 is in fluid flow engagement with hollow tubular portion 330 and with hollow vial puncturing spike 322. Hollow neck portion 344 terminates at a forward end thereof in a generally circular wall surface 346. The forward facing portion 348 is formed forward of neck portion 344. Forward facing portion 348 defines a central bore 354 which communicates between tubular portion 330 and a septum 350.

The user may simply push the vial adapter assembly 30 in the direction of the arrow in FIG. 1 into syringe adapter element 50. As seen in FIG. 2, this action causes housing element 500 to move rearward into the syringe adapter body 524, thereby causing needle 550 to puncture septum 350 and effect fluid communication from syringe 40, via needle 550 and spike 322, into vial 10. When the syringe 40 and vial 10 are connected and fluid can flow therebetween, the user may push plunger 42 inward, with the vial 10 positioned upright, thus injecting the fluid contained in syringe 40 into vial 10 and dissolving the drug contained therein. The user may then shake the drug mixing system to ensure that the drug in vial 10 is fully dissolved and that the resulting solution is homogenous.

The user may then turn the drug mixing system upside down and retract plunger 42, thus drawing at least part of the solution from the vial 10 into syringe 40. Subsequently, syringe 40 and syringe adapter element 50 may be disconnected. Septa 350 and 502 remain in touching relationship, while housing element 500 moves forward under action of the spring 536, until the needle tip returns to its resting position inside housing 500, thus preventing liquid spill.

As mentioned before, in accordance with embodiments of the present invention, a safety feature is provided that prevents exposure of the needle tip before the respective septa of the syringe adapter and fluid flow element have separated from each other. This safety feature may further ensure that no fluid drips outward when separating these parts from one another.

Figure 3A:
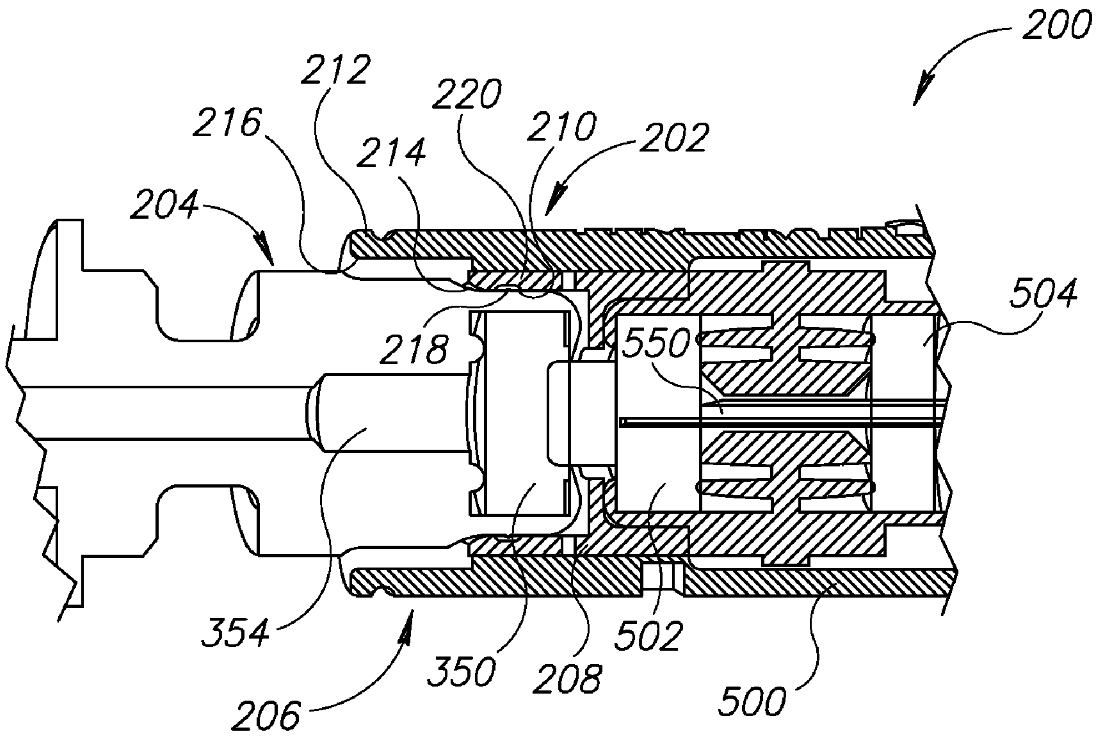
FIGS. 3A, 3B and 3C are simplified partially sectional illustrations of a syringe adapter element constructed and operative in accordance with an embodiment of the present invention, respectively, in a first position wherein the syringe adapter element is connected to a fluid flow adapter element, in a second position wherein the syringe adapter element is still connected to the fluid flow adapter element but resilient leaves can expand outward (or are already expanded prior to the insertion of the fluid flow adapter) to release the fluid flow adapter element, and a third position wherein the syringe adapter element has been separated from the fluid flow adapter element.
Figure 3B:
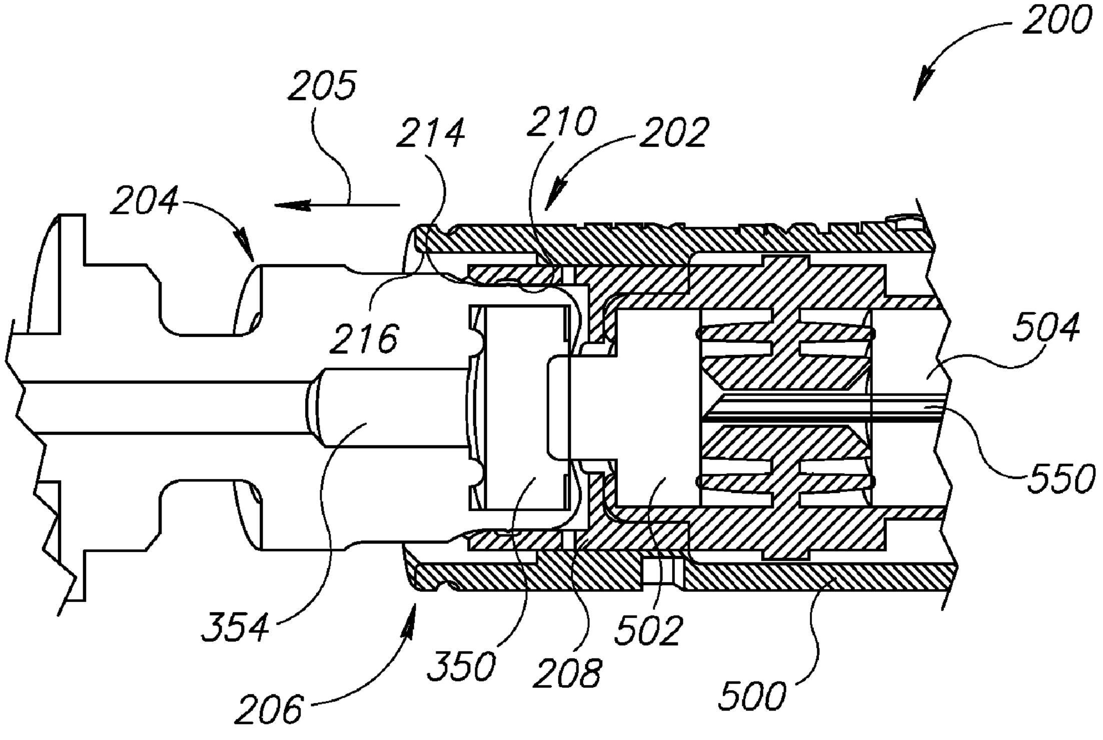
Figure 3C:
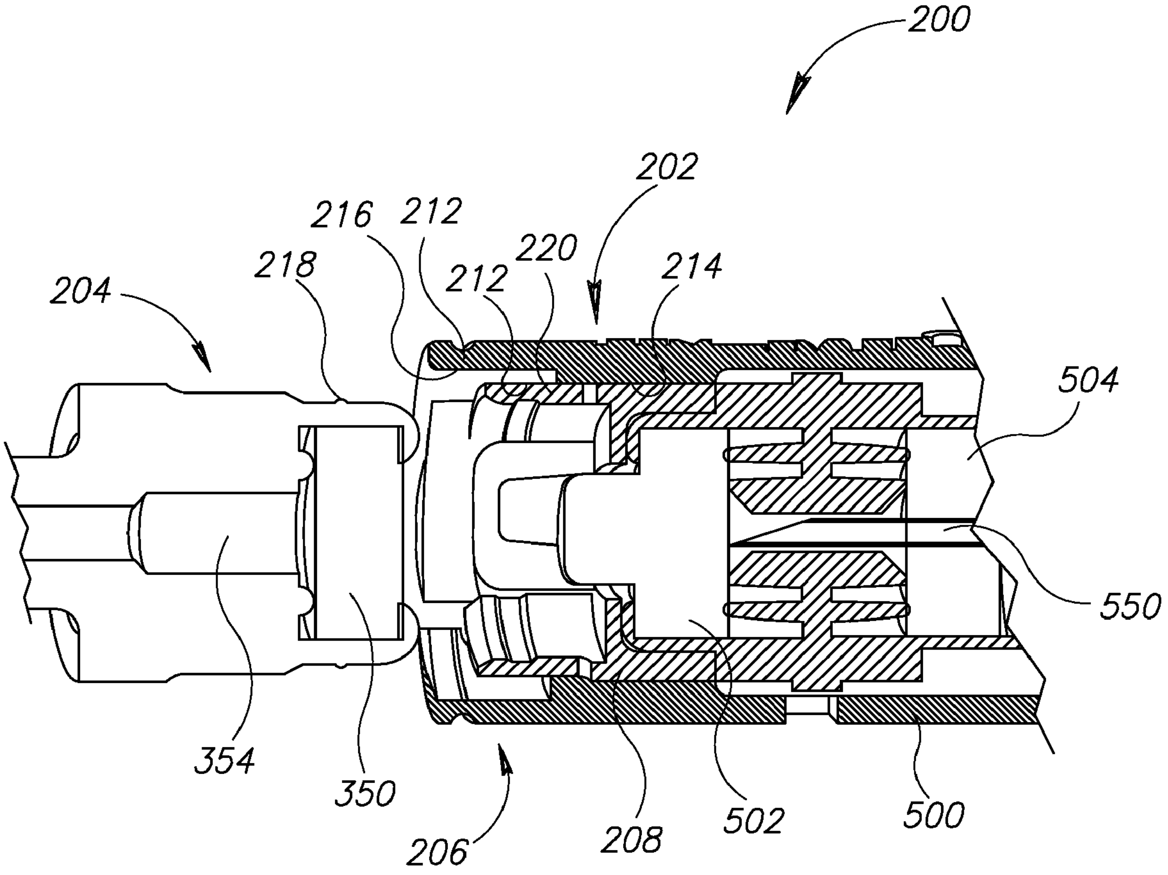

Reference is now made to FIGS. 3A-3C, which illustrate a syringe adapter element 200, constructed and operative in accordance with an embodiment of the present invention.

As similarly described hereinabove for syringe adapter element 50 (like elements being designated by like numerals), syringe adapter element 200 may include housing element 500 having syringe port 15 adapted for fluid connection with syringe 40 (15 and 40 not shown in FIG. 3A but may be the same as shown in FIG. 1 or 2), and a fluid port 202 adapted for fluid connection with a fluid flow adapter element 204 (such as, without limitation, a vial adapter element, a spike port adapter element or a needle port adapter element). Needle 550 and one or more septa 502 and 504 are disposed in housing element 500. As described above, needle 550 has a sealed orientation, corresponding to FIG. 1, wherein septum 502 blocks fluid flow through needle 550 and a fluid flow orientation, corresponding to FIG. 2, wherein needle 550 punctures septum 502 so as to permit fluid to flow through needle 550.

In accordance with an embodiment of the present invention, an anti-separation device 206 is adjacent fluid port 202. As will be described hereinbelow, when syringe adapter element 200 is connected to fluid flow adapter element 204, the anti-separation device 206 temporarily connects housing 500 to fluid flow element 204.

In the non-limiting illustrated embodiment, the anti-separation device 206 includes a ring member 208 with a plurality of resilient leaves 210 disposed inside a keeper element 212. Keeper element 212 (which is part of the syringe adapter) has a first bore 214 sized to prevent outward expansion of the resilient leaves 210 and a second bore 216, larger than the first bore 214, sized to permit outward expansion of the resilient leaves 210.

FIG. 3A shows a first position wherein syringe adapter element 200 is connected to fluid flow adapter element 204. The resilient leaves 210 resiliently fasten onto fluid flow adapter element 204. In the non-limiting illustrated embodiment, fluid flow adapter element 204 is formed with a ridge 218 adapted to fit in a groove 220 formed in the resilient leaves 210. The resilient leaves 210 are positioned in the first bore 214. They cannot expand outwards and hold onto the fluid flow adapter element 204.

Referring now to FIG. 3B, fluid flow adapter element 204 may be moved in the direction of an arrow 205 to a second position. In this position, the resilient leaves 210 are positioned in the second bore 216 and can expand outwards to release the fluid flow adapter element 204. In FIG. 3C, the syringe adapter element 200 has been separated from the fluid flow adapter element 204. In this manner, the septa 350 and 502 are forced into contact until the needle tip returns to its resting position inside housing 500. Therefore no liquid spill can occur irrespective of the speed at which the syringe adapter and fluid flow adapter are separated.

It is noted that in the first position, needle 550 can pierce septum 502, whereas in the second position, needle 550 cannot pierce septum 502.

Figure 4:
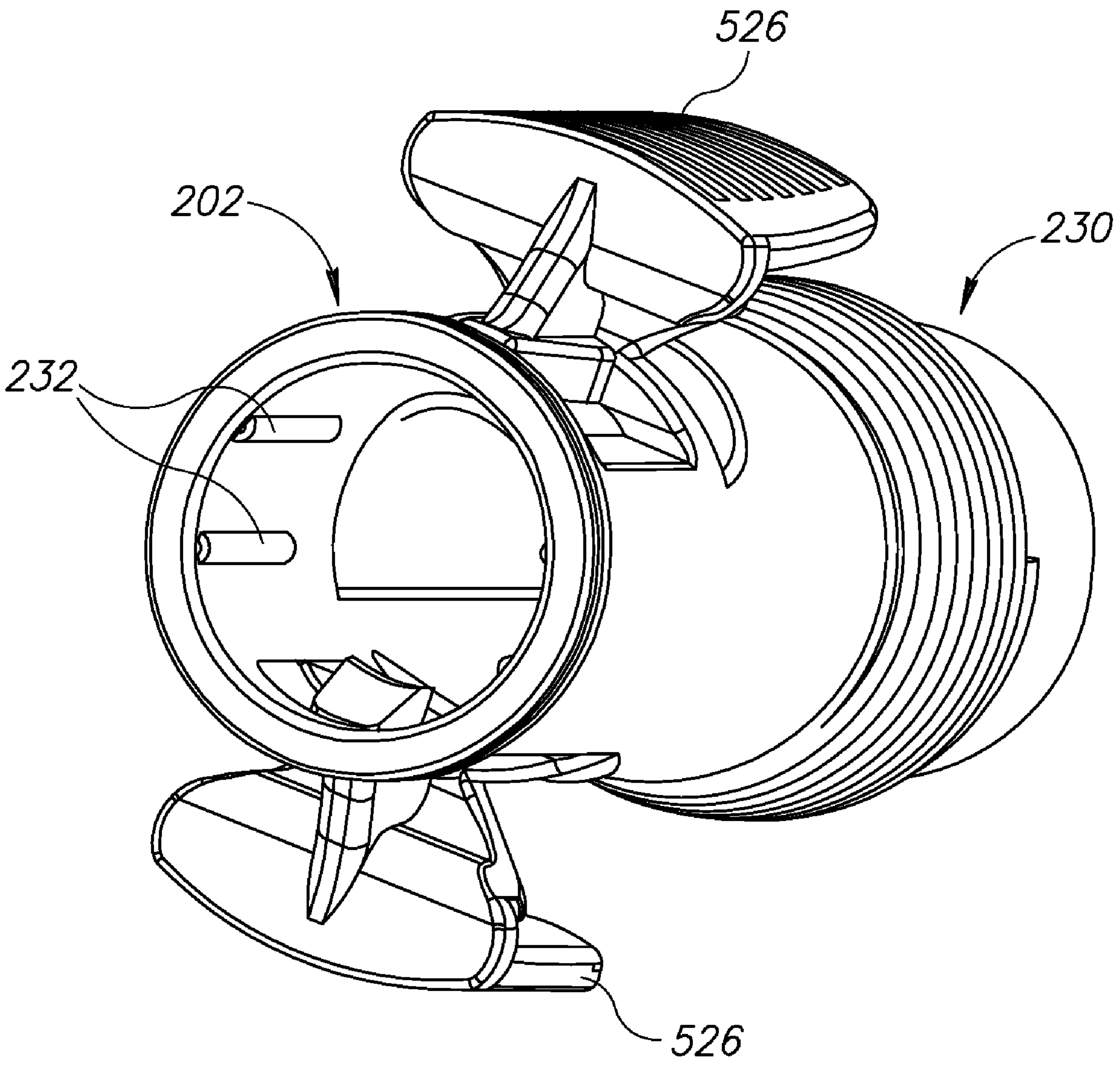
FIG. 4 is a simplified partially cutaway illustration of a syringe adapter element constructed and operative in accordance with another embodiment of the present invention, wherein the syringe adapter element has inwardly facing protrusions adapted to apply a friction force.

Reference is now made to FIG. 4, which illustrates a syringe adapter element 230, constructed and operative in accordance with another embodiment of the present invention. In this embodiment, syringe adapter element 230 has inwardly facing protrusions 232 that "tighten" the grip of fluid port 202 on the fluid flow adapter element 204. In other words, the inwardly facing protrusions 232 apply a friction seizing force on the fluid flow adapter element 204 as it is pulled out of fluid port 202, thereby preventing rapid and sudden separation of the fluid flow adapter element 204 from the syringe adapter element 200.

Figure 5A:
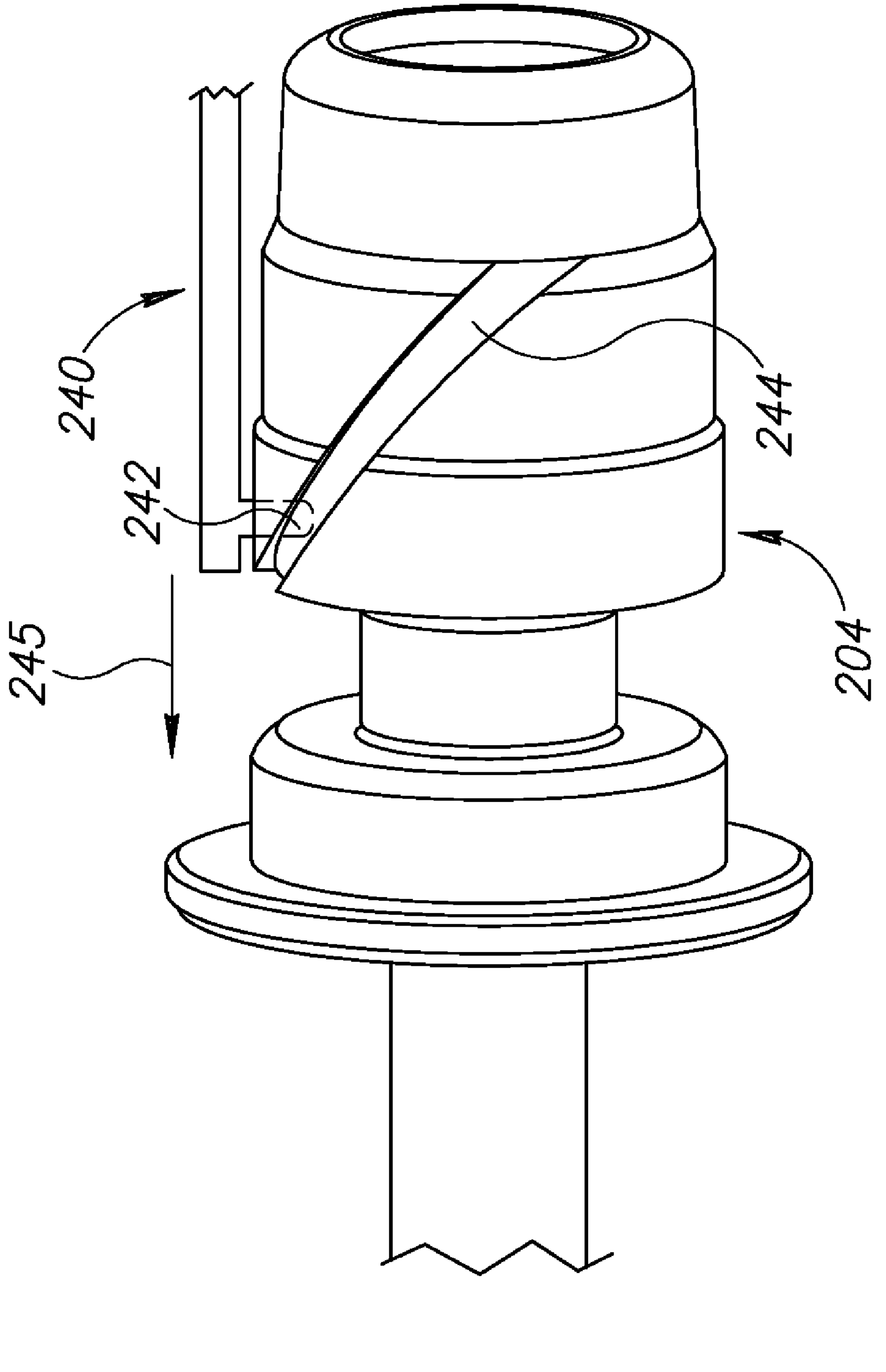
FIGS. 5A, 5B and 5C are simplified illustrations of a syringe adapter element constructed and operative in accordance with yet another embodiment of the present invention, wherein the connection between the syringe adapter element and the fluid flow adapter element comprises a tooth that fits in a non-straight channel.
Figure 5B:
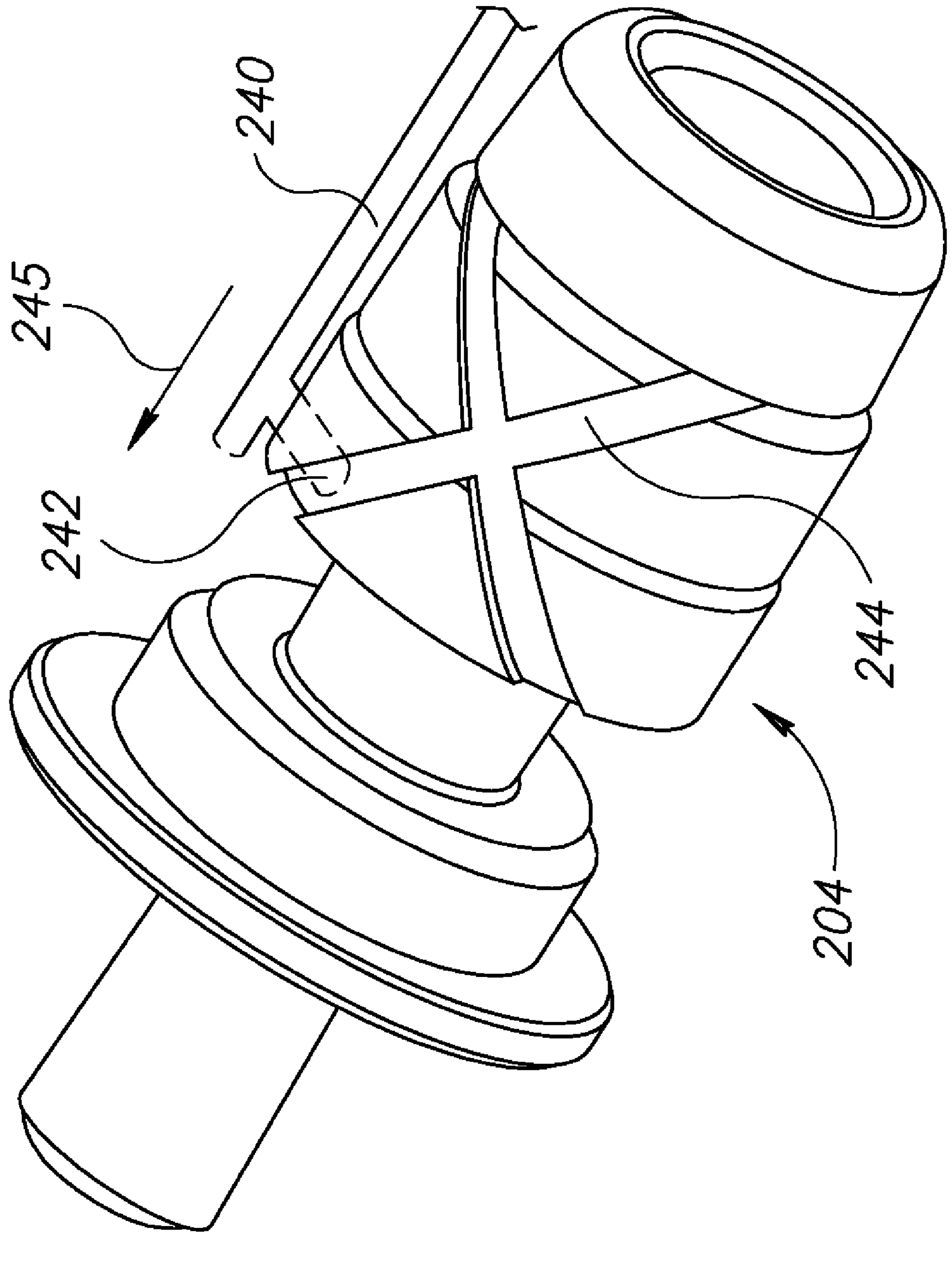
Figure 5C:
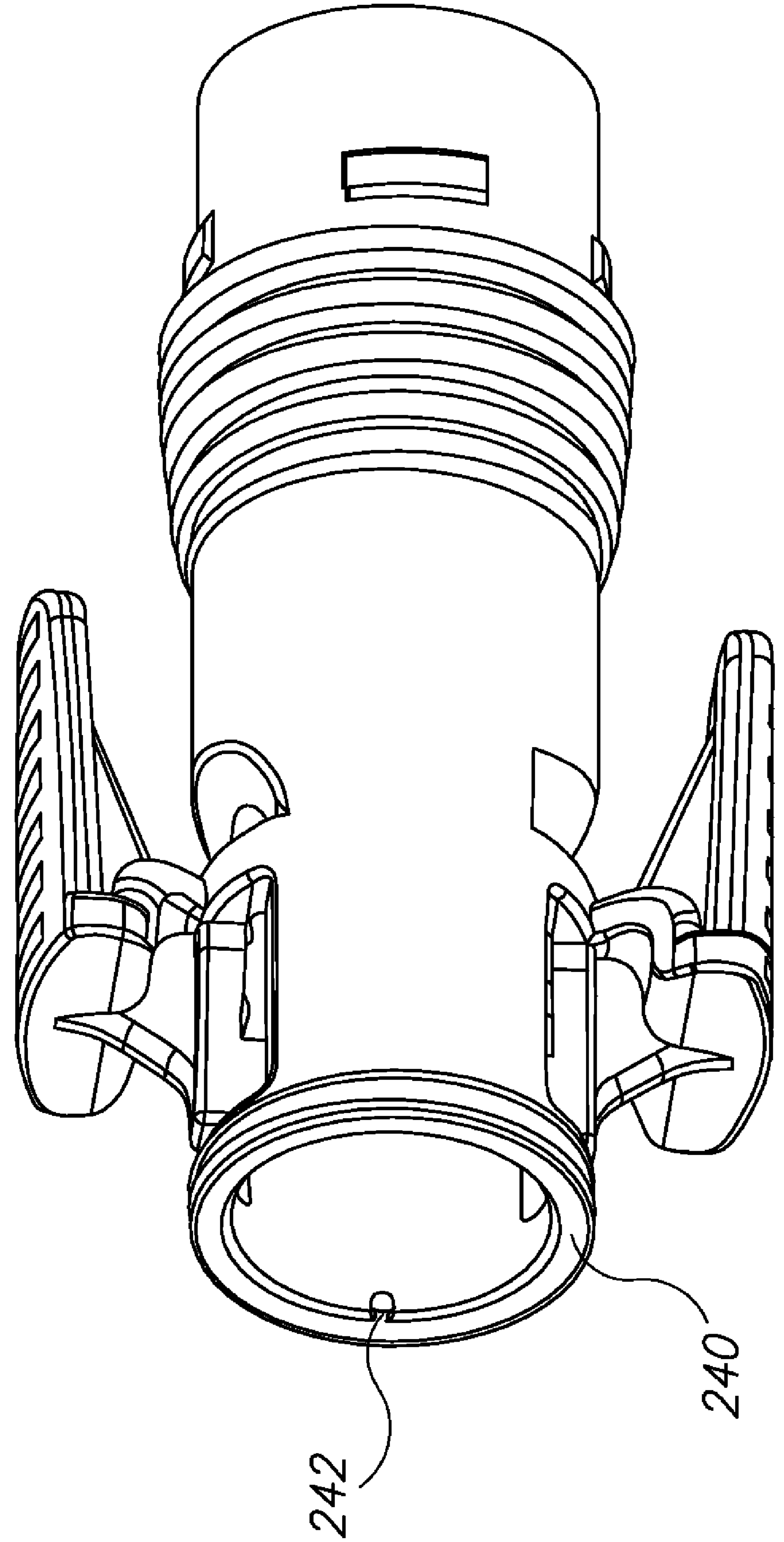

Reference is now made to FIGS. 5A, 5B and 5C, which illustrate a syringe adapter element 240, constructed and operative in accordance with yet another embodiment of the present invention. In this embodiment, the connection between the syringe adapter element 240 and the fluid flow adapter element 204 comprises a tooth 242 that fits in a non-straight channel 244. For example, fluid flow adapter element 204 may be formed with a spiral channel or channels 244 that mates with one or more teeth 242 on syringe adapter element 240. (Alternatively, syringe adapter element 240 may be formed with spiral channel 244 and fluid flow adapter element 204 may include teeth 242.) When an axial force in the direction of arrow 245 is applied to separate syringe adapter element 240 and fluid flow adapter element 204, the action of the tooth or teeth 242 moving in the non-straight channel 244 works against this axial force, thereby preventing premature separation of the fluid flow adapter element 204 from the syringe adapter element 200.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A syringe adapter element for use in a drug mixing system comprising:

a housing element having a syringe port adapted for fluid connection with a syringe and a fluid port adapted for fluid connection with a fluid flow adapter element;

a needle and at least one septum disposed in said housing element, said needle having a sealed orientation wherein said at least one septum blocks fluid flow through said needle and a fluid flow orientation wherein said needle punctures said at least one septum so as to permit fluid to flow through said needle; and an anti-separation device adjacent said fluid port, such that when said syringe adapter element is connected to a fluid flow adapter element, said anti-separation device applies a force that acts against separating said syringe adapter element from the fluid flow adapter element, wherein said anti-separation device comprises a ring member with a plurality of resilient leaves disposed inside a keeper element, said keeper element having a first bore sized to prevent outward expansion of said resilient leaves and a second bore, larger than the first bore, sized to permit outward expansion of said resilient leaves, said resilient leaves being adapted to resiliently fasten onto a fluid flow adapter element, said anti-separation device having first and second positions, wherein in the first position, said resilient leaves are positioned in said first bore and are adapted to hold onto the fluid flow adapter element, and in the second position, said resilient leaves are positioned in said second bore and are adapted to expand outward to release the fluid flow adapter element, and wherein said resilient leaves move together with said fluid flow adapter element with respect to said syringe adapter element.

2. The syringe adapter element according to claim 1, wherein in the first position, said needle can pierce said at least one septum, and in the second position, said needle cannot pierce said at least one septum.

3. The syringe adapter element according to claim 1, further comprising a fluid flow adapter element formed with a ridge adapted to fit in a groove formed in said resilient leaves when said syringe adapter element is connected to said fluid flow adapter element.

4. The syringe adapter element according to claim 1, wherein said anti-separation device comprises a plurality of inwardly facing protrusions formed on an inner perimeter of said fluid port adapted to apply a friction force against a fluid flow adapter element inserted in said fluid port.

5. The syringe adapter element according to claim 1, further comprising a fluid flow adapter element, and wherein said anti-separation device comprises a non-straight channel formed in one of the syringe adapter and fluid flow adapter elements that interfaces with a tooth formed in the other of the syringe adapter and fluid flow adapter elements, wherein a straight force applied to separate the syringe adapter and fluid flow adapter elements is acted against by said tooth moving in said non-straight channel.

6. The syringe adapter element according to claim 1, wherein said resilient leaves are cantilevered along an axial length of said syringe port.

* * * * *